(12) United States Patent
Laguna

(10) Patent No.: US 7,335,184 B2
(45) Date of Patent: Feb. 26, 2008

(54) BALLOON CATHETER AND TREATMENT APPARATUS

(75) Inventor: Alvaro J. Laguna, Flagstaff, AZ (US)

(73) Assignee: Sentient Engineering and Technology, Flagstaff, AZ (US)

( * ) Notice: Subject to any disclaimer, the term of this patent is extended or adjusted under 35 U.S.C. 154(b) by 512 days.

(21) Appl. No.: 10/655,665

(22) Filed: Sep. 5, 2003

(65) Prior Publication Data

US 2004/0098021 A1    May 20, 2004

Related U.S. Application Data

(63) Continuation-in-part of application No. 10/187,923, filed on Jul. 2, 2002, now Pat. No. 6,773,447.

(51) Int. Cl.
*A61M 29/00* (2006.01)
(52) U.S. Cl. .................................. 604/101.02
(58) Field of Classification Search ........ 606/192–198; 604/96.01, 101.01, 61.02, 101.03; 428/36.01, 428/36.2, 36.3, 36.5, 36.1, 36.02, 36.03, 428/36.05
See application file for complete search history.

(56) References Cited

U.S. PATENT DOCUMENTS

| | | | |
|---|---|---|---|
| 4,637,396 A * | 1/1987 | Cook | 604/103 |
| 4,702,252 A * | 10/1987 | Brooks et al. | 604/103 |
| 5,019,042 A | 5/1991 | Sahota | |
| 5,499,980 A | 3/1996 | Euteneuer | |
| 5,718,973 A * | 2/1998 | Lewis et al. | 428/36.3 |
| 5,833,657 A | 11/1998 | Reinhardt et al. | |
| 6,132,824 A | 10/2000 | Hamlin | |
| 6,520,933 B1 * | 2/2003 | Evans et al. | 604/103.07 |
| 6,585,926 B1 | 7/2003 | Mirzaee | |
| 6,695,809 B1 * | 2/2004 | Lee | 604/96.01 |
| 2002/0165523 A1 | 11/2002 | Chin et al. | |
| 2003/0074016 A1 | 4/2003 | Campbell et al. | |

FOREIGN PATENT DOCUMENTS

WO    WO 2004/004820 A1    1/2004

\* cited by examiner

*Primary Examiner*—Kevin T. Truong
(74) *Attorney, Agent, or Firm*—Greenberg Traurig LLP

(57) ABSTRACT

A balloon catheter. The balloon is of a composite material having the flexibility and elastic characteristics of an elastomeric material, yet exhibiting the growth limits of inelastic materials. The balloon may be provided in various shapes. The balloon may be treated to maintain a substantially constant length during inflation and deflation. The balloon may be provided with regions of porosity for the delivery of therapeutic agents, and may be treated to exhibit regions of distinct compliance. Also disclosed is an apparatus, which may be used to impart the regions of distinct compliance into the balloon.

93 Claims, 11 Drawing Sheets

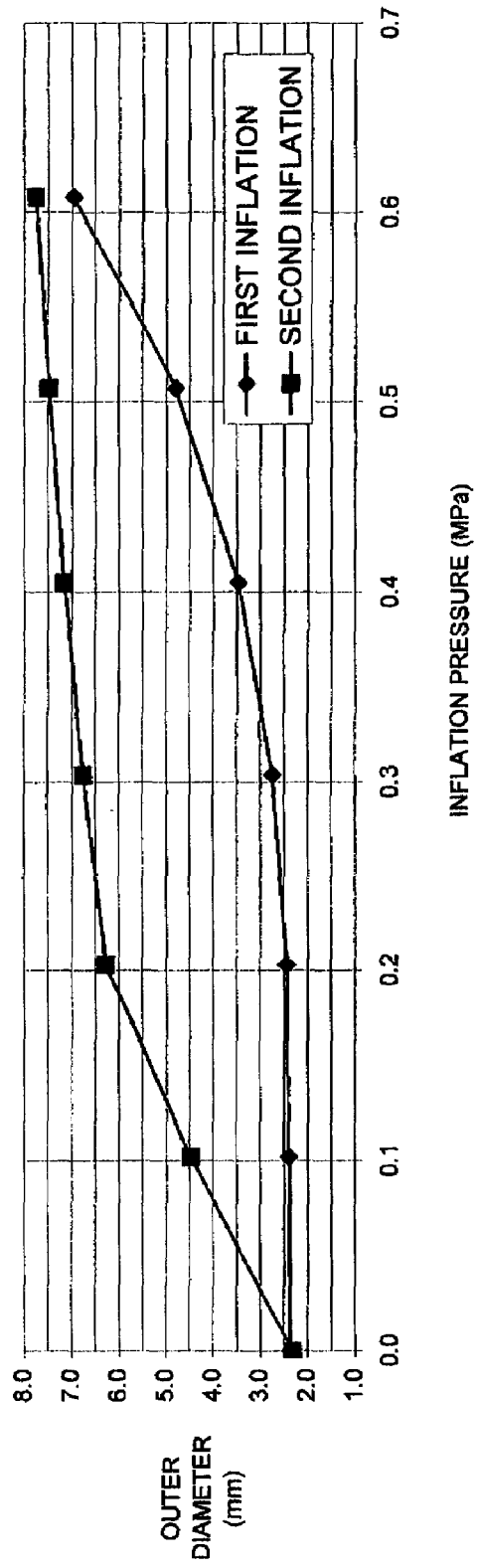

BALLOON CATHETER AND TREATMENT APPARATUS

RELATED APPLICATION

This application claims the benefit of and is a continuation-in-part of U.S. application Ser. No. 10/187,923, filed Jul. 2, 2002, now U.S. Pat. No. 6,773,447 which is incorporated herein by reference in its entirety.

BACKGROUND

This application generally relates to balloon catheters. In this regard, various types of balloon catheters are routinely employed in medical procedures. Typically, balloon catheters consist of elongate, thin-walled tubular catheter assemblies with an inflatable balloon attached at the distal end.

Balloon catheters are commonly used to dilate or remove constrictions, or to deliver and deploy other devices within bodily conduits. In the treatment of constricted conduits, the balloon catheter is inserted within the patient and navigated through the conduit (such as a blood vessel) to the site of blockage. The balloon at the distal end of the catheter is then inflated, causing the balloon to increase in diameter until the desired therapeutic result is achieved. Once the blockage is opened, the balloon is deflated and removed from the patient.

In a similar fashion, devices such as stents are typically secured onto the distal ends of balloon catheters, the catheters being used to deliver the stent to the site of a blockage. Once at the desired location, the underlying balloon is inflated, causing the stent to increase in diameter and thus remodel and support the tissue, which constitutes the blockage within the bodily conduit. Once the therapeutic result is achieved the balloon is deflated and removed from the patient, leaving the stent implanted.

Balloon catheters may employ various balloon materials depending on the application for which they are used. For example, embolectomy balloon catheters utilize elastomeric balloon materials such as latex or silicone because, in such procedures, there is no need for the use of high inflation pressures. Angioplasty balloon catheters, on the other hand, utilize relatively inelastic materials such as polyester or nylon because in such procedures the application of high inflation pressure is often required.

Elastomeric and inelastic balloon materials each have advantages and drawbacks. While elastomeric materials are generally soft and conformable, they lack strength and exhibit continuous diameter growth with the application of increasing inflation pressure until rupture occurs. Elastomeric balloon materials are referred to as compliant. Inelastic balloon materials have very predictable diameter growth characteristics, and distend very little beyond their intended diameter with the application of increasing inflation pressure. Inelastic balloon materials are referred to as non-compliant or semi-compliant depending on their stiffness.

Due to their stiffness, inelastic balloon materials are not soft and conformable. Balloons made of these materials, such as angioplasty balloons, are carefully wrapped into a small cross-sectional configuration prior to introduction into the patient. During inflation, the balloons unwrap and assume their intended diameters. During subsequent deflation, however, the balloons do not return to their initial small cross-sectional state.

Angioplasty balloons are often difficult to maneuver through tortuous bodily conduits, posing a challenge in the treatment of blockages within small conduits such as within the coronary vasculature or the neurovasculature. Further, when inflated within a curved conduit, such balloons tend to straighten the conduit because of their lack of conformability. This straightening can result in localized trauma.

The delivery of devices such as stents via angioplasty balloon catheters can be problematic due to inadequate securement of the stent onto the balloon. The inelastic materials do not provide adequate engagement to the stent, leaving the stent prone to slipping along the length or completely off of the balloon. Also, because the inelastic materials are essentially non-compressible, the edges of a stent, when mounted onto a balloon made of such materials, are exposed and vulnerable to being damaged during navigation through narrowed tortuous conduits.

In addition to the drawbacks mentioned above, there are complications associated with the mechanics of folded balloons. As described, angioplasty balloons are typically folded or wrapped about the catheters to which they are attached. During use, the balloons unfold at very low pressure. In the presence of an obstruction within a conduit, particularly if the obstruction is centered within the length of the balloon, such balloons tend to unfold very quickly at the ends where diameter growth is unimpeded, forming an hourglass shape. As the balloon is inflated to greater pressures, the obstructive tissue is remodeled toward the center of the balloon length, creating a densified lesion and a generally insufficient vessel inner diameter. Similar mechanics may occur during inflation of a stent, particularly if the length of the stent is not carefully matched to the length of the balloon.

In many cases, blockages occur close to the junction of two conduits. In such situations, particularly if the lesion is located at one end of the balloon, the mechanics described above, rather than densifying the obstructive tissue towards the center of the balloon, redistribute the occlusive tissue into the junction between the two conduits, thus compromising the junction and creating an obstruction within the branching conduit.

Another complication of balloon angioplasty and stenting is the formation of emboli. Embolic episodes occurring in various anatomical locations, particularly the brain can result in potentially debilitating outcomes or even death.

SUMMARY

An improved balloon catheter is described comprised of a composite balloon material attached to a catheter assembly. The balloon material has the flexibility and elastic characteristics of an elastomeric material, but also has a well-defined growth limit such as exhibited by inelastic balloon materials. The balloon material may be manufactured to maintain a substantially constant length during inflation and subsequent deflation. Various embodiments of the balloon material may be produced to be liquid tight or may be produced with one or more regions of porosity through which various therapeutic agents may be delivered. Additionally, the balloon material may be manufactured with regions of distinct inflation characteristics (compliance) such that one or more regions of the balloon inflate at a faster rate than the remaining region(s). Regions of distinct compliance provide enhanced control during angioplasty and stenting procedures and may be beneficial in reducing the creation of emboli during such procedures. The balloon catheter may also be provided with a balloon having a substantially constant diameter or may be provided with a balloon having a predetermined shape to further enhance angioplasty and stenting procedures.

Also disclosed is an apparatus, which may be used to instill the regions of distinct compliance within the balloon. The apparatus may be used to essentially customize the compliance of the balloon such that the balloon optimally serves the needs of the end user.

A better understanding of the objects, advantages, features, properties and relationships of the disclosed balloon catheter and related apparatus will be obtained from the following detailed description and accompanying drawings which are indicative of the various ways in which the principles thereof may be employed.

BRIEF DESCRIPTION OF EXEMPLARY DRAWINGS

For a better understanding of the disclosed balloon catheter and related apparatus, reference may be had to a preferred embodiment shown in the following drawings in which.

Figure 4A:
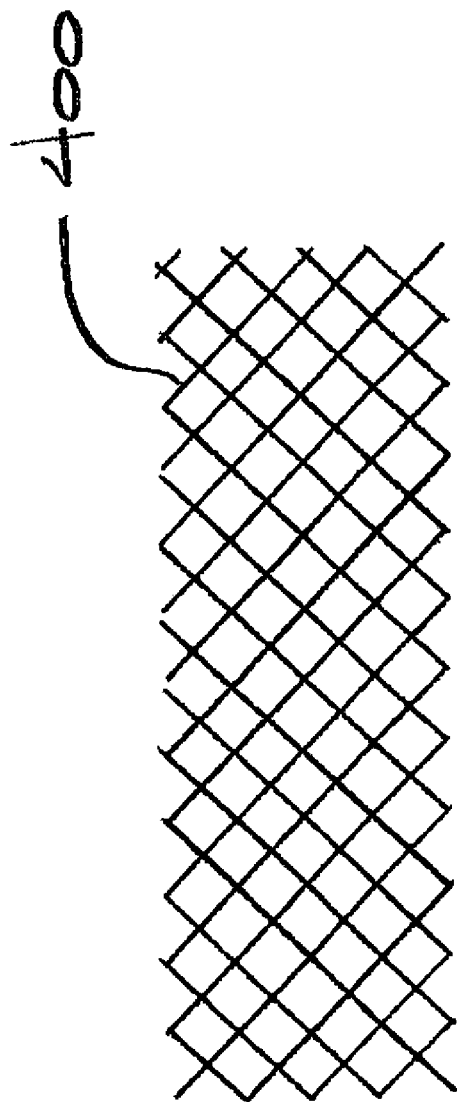
Figure 4B:
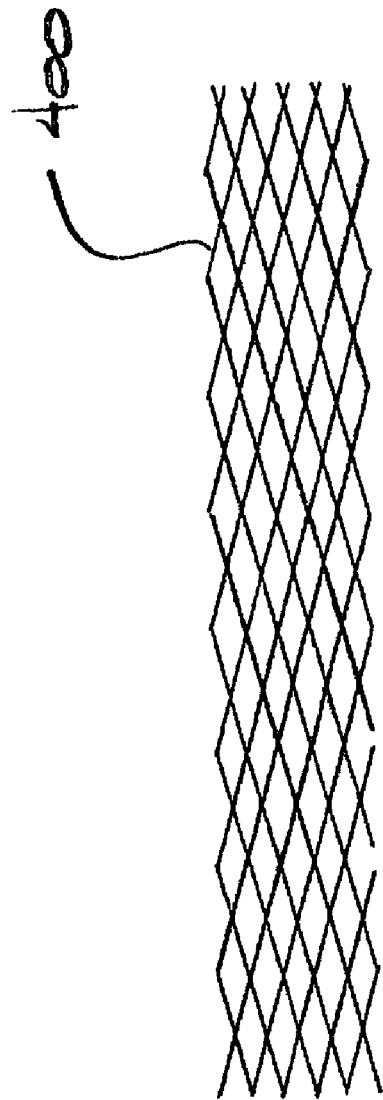
Figure 4C:
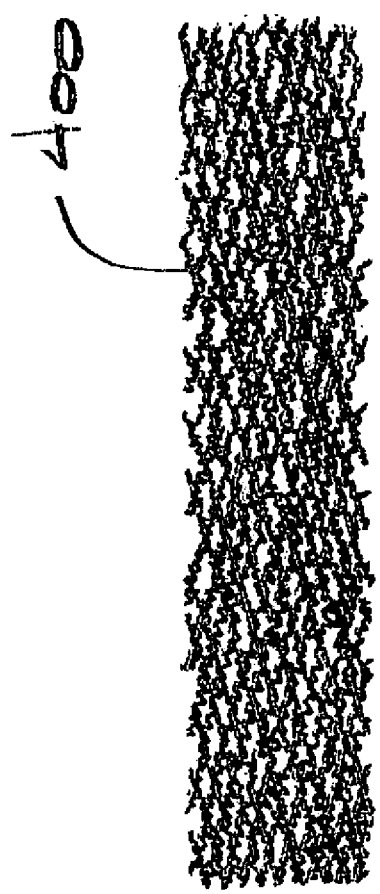
Figure 6A:
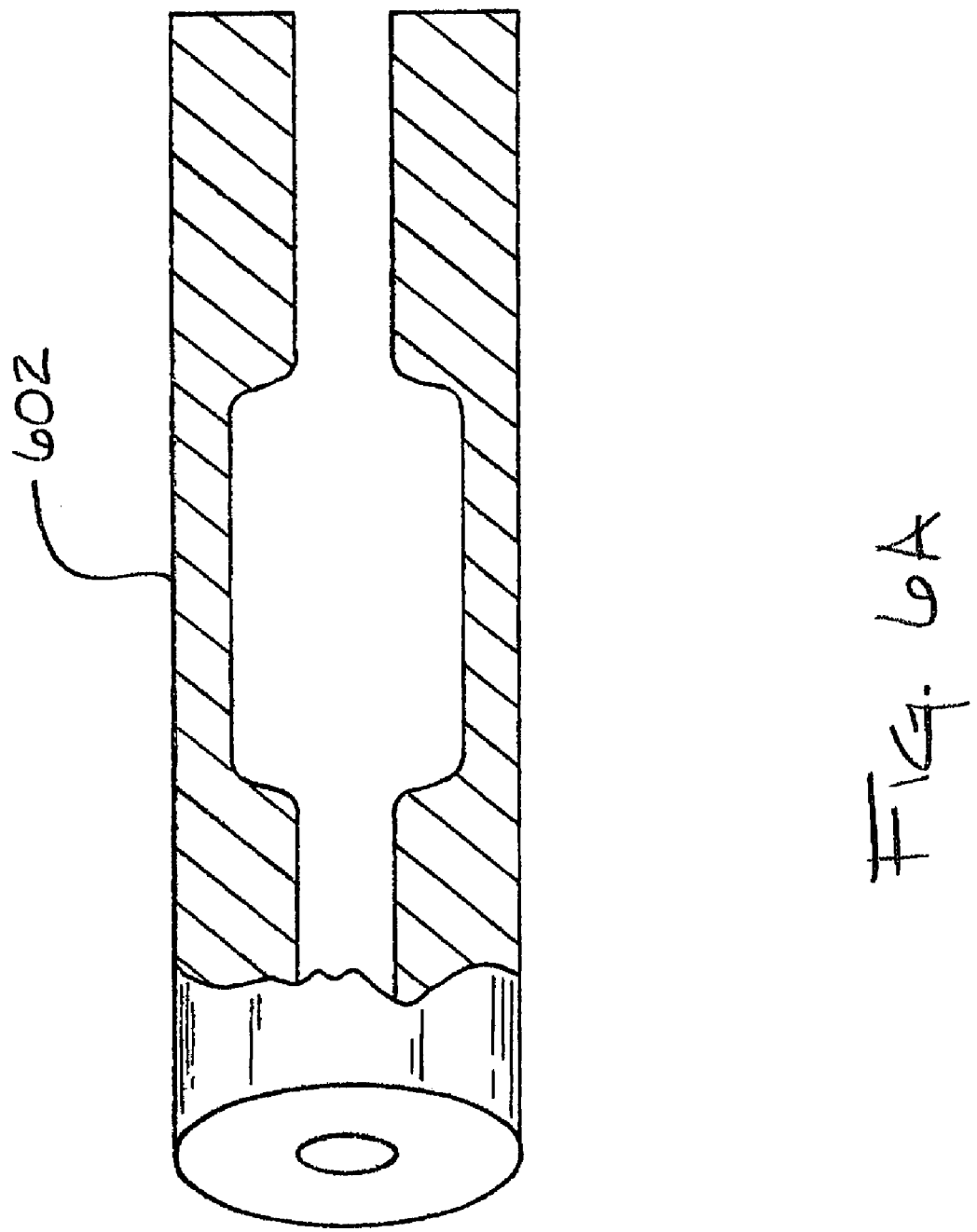
Figure 6B:
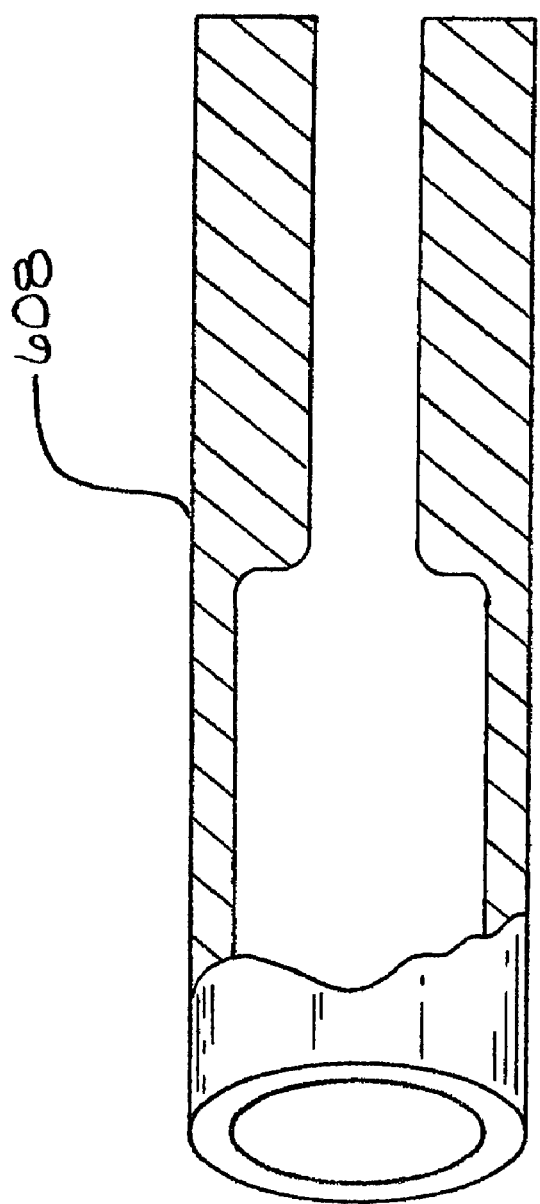
Figure 6:
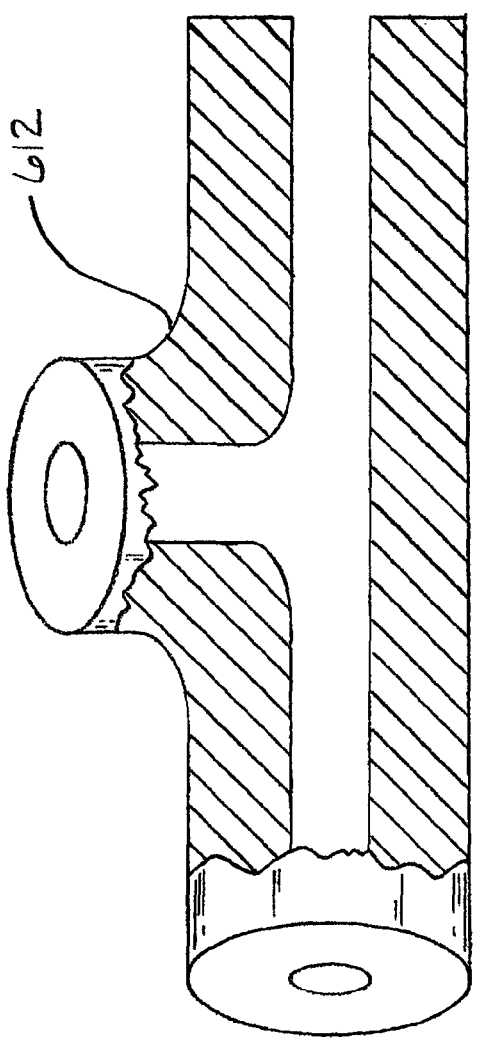
Figure 7:
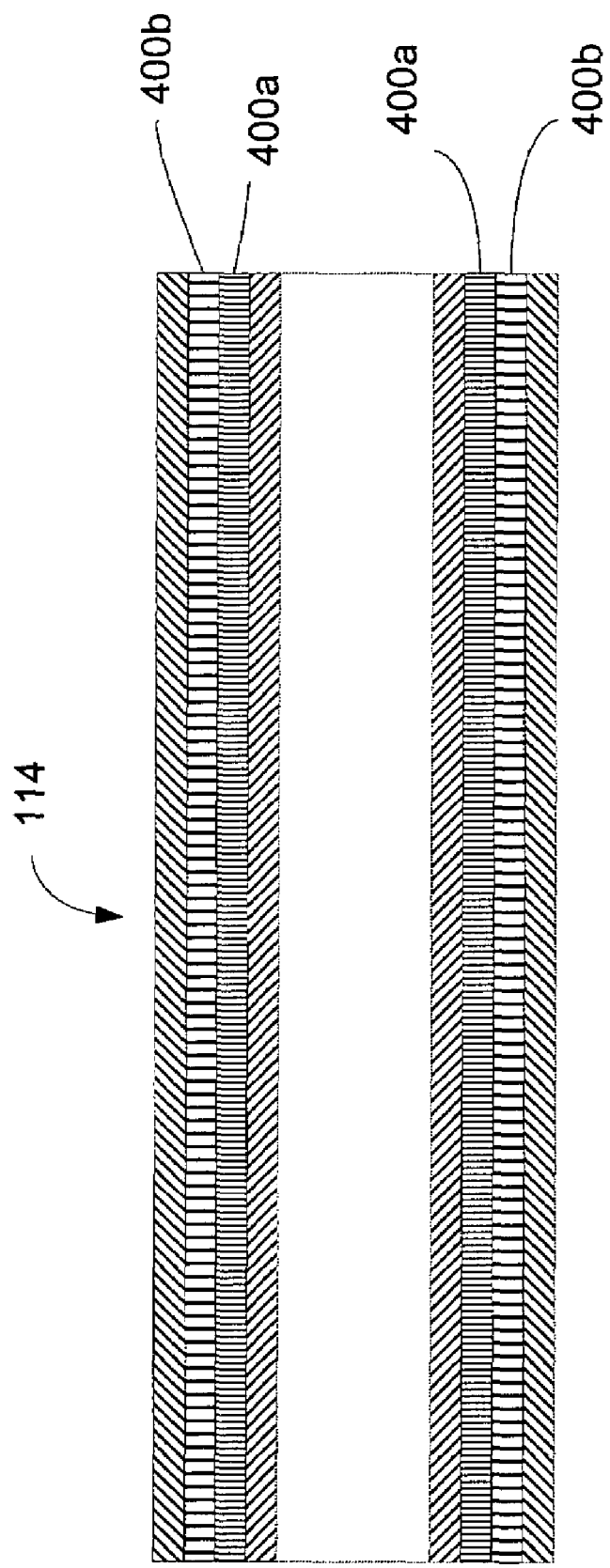

FIGS. 4A, 4B, and 4C are enlarged views of a braided tube used in the manufacture of an exemplary balloon material;

FIG. 5 is a graph illustrating the compliance characteristics of an exemplary balloon material;

FIGS. 6A, 6B and 6C are partial longitudinal cross-sectional views of exemplary inflation molds that may be used to customize the compliance characteristics of exemplary balloon material; and FIG. 7 is an enlarged longitudinal cross-sectional view of an exemplary balloon material.

DETAILED DESCRIPTION

Figure 1:
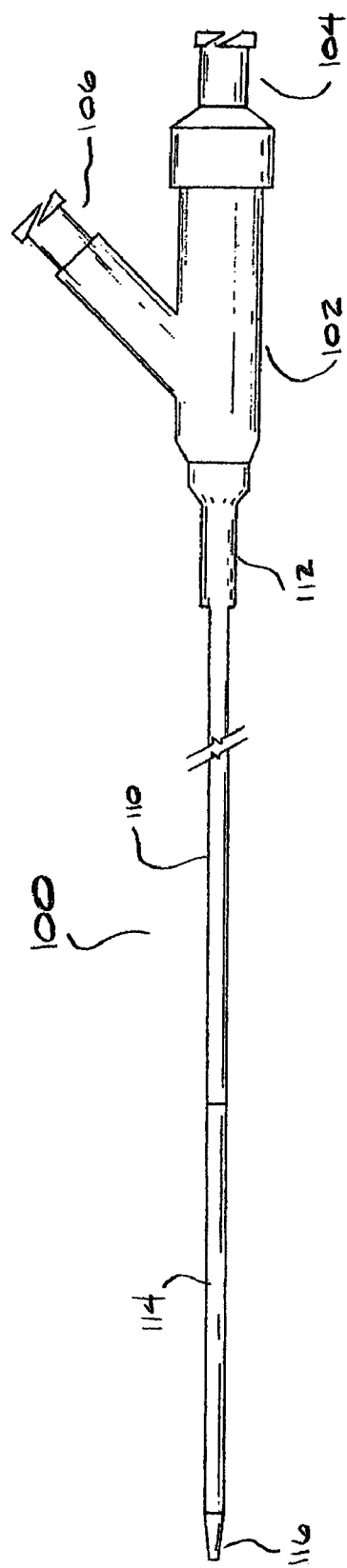
FIG. 1 is an elevational view of an exemplary balloon catheter.

Referring to the figures, wherein like numerals designate like elements, illustrated in FIG. 1 is an exemplary balloon catheter 100 that includes a proximal adapter 102 located at the proximal end of the device. The proximal adapter includes a wire port 104 and a balloon port 106, both of which comprise a luer fitting for engagement with other accessory devices. In the illustrated example, the proximal adapter 102 is attached to an inner catheter member 108 (see FIG. 2) and an outer catheter member 110. The two catheter members are arranged coaxially. The attachment between the proximal adapter 102 and the outer catheter member 110 may be enhanced by strain relief member 112, which provides support to the outer catheter member 110, minimizing the tendency of the outer catheter member 110 to kink at or near the attachment point.

Figure 2:
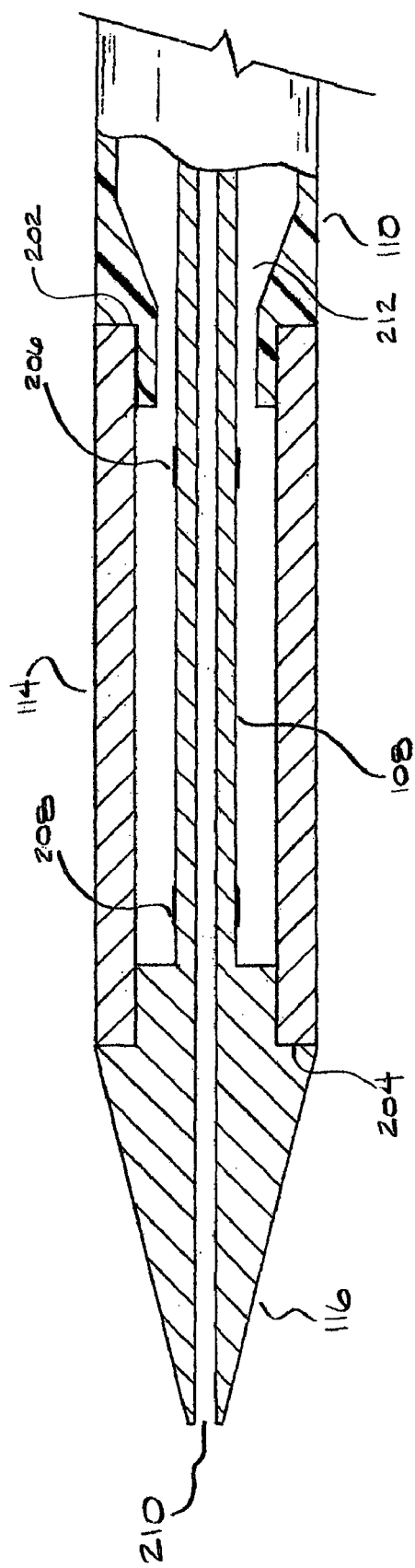
FIG. 2 is an enlarged partial longitudinal cross-sectional view of the distal portion of an exemplary balloon catheter.

At the distal portion of the balloon catheter 100 is balloon 114. Balloon 114 is attached at its proximal end to outer catheter member 110 and at its distal end to inner catheter member 108 as illustrated in FIG. 2. Also, at the distal portion of balloon catheter 100 is distal tip 116, which comprises the distal end of inner catheter member 108.

Although the exemplary balloon catheter depicted by FIG. 1 comprises two catheter members arranged coaxially, any suitable catheter member arrangement may be employed. For example, a single, dual-lumen catheter member, having a lumen providing communication between the balloon port and the balloon, and another lumen capable of accommodating a guidewire may be employed. Additionally, the assembly of the catheter member(s) may be of any suitable configuration such as, but not limited to, fixed wire, wherein a wire element is included into the catheter tube(s) to add stiffness, over the wire (as depicted, for example, in FIG. 1), or rapid exchange.

The design and manufacture of catheter components and assemblies thereof is well known. Catheter members 108 and 110 may be of any suitable material or combination of materials such as, but not limited to, silicone, polyurethane, nylon, polyethylene, various copolymers such as PolyEther Block Amid (PEBA), or polytetrafluoroethylene (PTFE). In some instances catheter members 108 and 110 may suitably contain metallic elements such as, but not limited to, braids, hypodermic tubing and/or wires. Proximal adapter 102 may be configured in any suitable manner and may also be of any suitable material or combination of materials such as, but not limited to, nylon, polycarbonate, polypropylene, PEBA, or polysulfone. Any suitable method may be employed to create the attachments between the various elements of the balloon catheter 100. Such methods may include, but are not limited to, the use of various adhesives or thermal bonding techniques.

Turning to FIG. 2, there is illustrated an enlarged view of an arrangement of catheter members 108 and 110 as well as balloon 114 of an exemplary balloon catheter 100. In this illustrated example, the distal end of outer catheter member 110 is provided with a step 202 which accommodates the proximal end of balloon 114 such that the outer surface of balloon 114 is flush with the outer surface of the outer catheter member 110. In a similar fashion, inner catheter member 108 is provided with step 204 which accommodates the distal end of balloon 114 such that the outer surface of balloon 114 is flush with the outer surface of distal tip 116 of the inner catheter member 108. Such an arrangement may be used to create a sleek profile to enhance navigation of the balloon catheter 100 through narrow, tortuous bodily conduits.

As shown by FIG. 2, inner catheter member 108 may be provided with radiopaque markers 206 and 208. These markers can be positioned so as to coincide with the edges of balloon 114 while the balloon is inflated, and to provide radiographic visualization of the balloon. Markers 206 and 208, in this example configuration, are arranged as bands attached to inner catheter member 108. Any suitable arrangement of markers 206 and 208 may be employed. Additionally, any suitable method of attaching the markers 206 to the inner catheter member 108 such as, but not limited to, the use of various adhesives, or swaging may be used. Also, markers 206 and 208 may be of any suitable material or combination of materials such as, but not limited to, gold, tantalum, or alloys of platinum and iridium. Markers 206 and 208 may also be printed onto inner catheter member 108 with radiopaque inks.

Inner catheter member 108 may also include a lumen 210, which may further accommodate a guidewire to aid in navigation of the balloon catheter 100. In the illustrated, exemplary balloon catheter, lumen 210 extends along the entire length of inner catheter member 108. Guidewire port 104 provides convenient access to lumen 210. Similarly, outer member 110 includes lumen 212, which provides communication between balloon port 106 and balloon 114 allowing balloon 114 to be inflated with, for example, saline or water.

Figure 3:
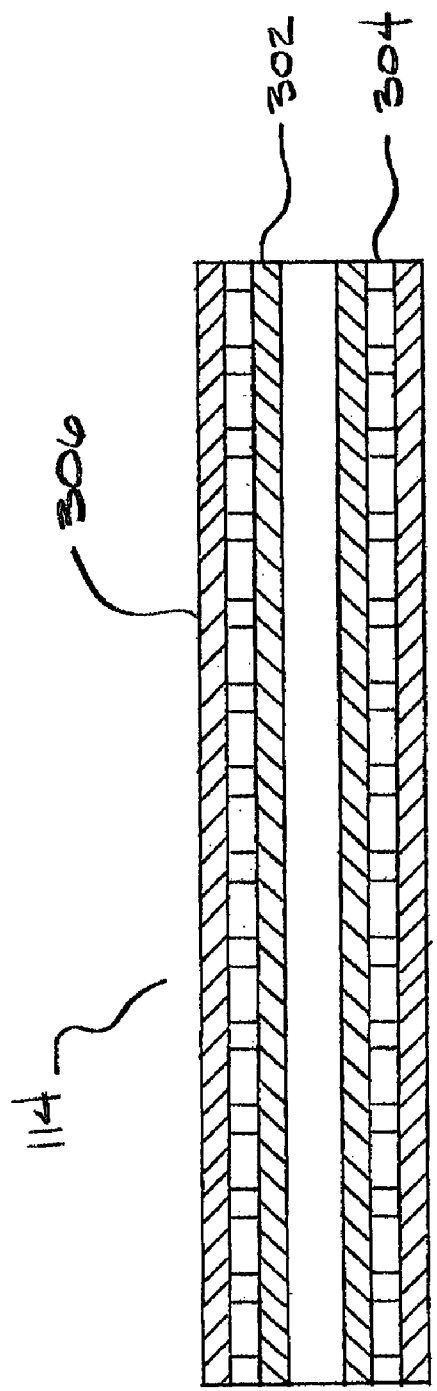
FIG. 3 is an enlarged longitudinal cross-sectional view of an exemplary balloon material.

Turning now to FIG. 3, there is depicted an enlarged cross-sectional view of an exemplary balloon 114. While the illustrated, exemplary balloon 114 comprises 3 layers, it is to be understood, however, that balloon 114 may comprise any suitable number of layers in any suitable manner. It is to be further understood that the layers need not be separate and distinct. Rather, the layers can be co-extruded. In the illustrated, exemplary balloon 114, inner layer 302 is comprised of silicone tubing having an inner diameter of approximately 1.2 mm and an outer diameter of approximately 1.4 mm.

To produce the exemplary balloon 114, an approximately 150 mm length of silicone tubing may be fitted coaxially onto an approximately 1.19 mm diameter stainless steel rod. Isopropyl alcohol may be used as a lubricant to facilitate the fitting. With the silicone tubing fitted onto the rod, the rod is preferably placed within an air convection oven set at approximately 70° C. for approximately 10 minutes to evaporate any residual alcohol. While the illustrated inner layer 302 is comprised of silicone tubing and is liquid tight, any suitable material or combination of materials such as, but not limited to, latex, polyurethane, PEBA, and/or fluoroelastomers may be used. Furthermore, inner layer 302 may include regions of porosity that allow the passage of fluids there through while still allowing balloon 114 to be inflated. Various methods or combinations of methods may be employed to create a suitable inner layer 302. Such methods include, but are not limited to, dipping, application by spraying, and/or molding.

In this illustrated example balloon 114, the middle layer 304 comprises 2 layers of a treated braided tube 400. The 2 layers of treated braided tube 400 are intended to provide strength to the finished embodiment of balloon 114 such that the balloon achieves a well-defined inflation diameter beyond which minimal growth occurs. A suitable braided tube 400 is manufactured by Prodesco, Inc. of Perkasie, Pa. (now Secant Medical, LLC). The tube is created from 144 individual strands of 9 denier monofilament polyester yarn, has a relaxed inner diameter of approximately 7 mm, a wall thickness of approximately 0.05 mm, and a braid density of 21.7 pixels per centimeter (55 pixels per inch).

Turning to FIG. 4A, there is now illustrated an enlarged view of the braid pattern of braided tube 400 in a relaxed state. While the illustrated example utilizes polyester braid material, any suitable material or combination of materials such as, but not limited to, nylon, polyethylene, carbon, kevlar, PEBA, and/or PTFE may be used. In some embodiments it may be advantageous to combine thin metallic elements into the braid. Additionally, any suitable braid pattern with any suitable strand of any suitable denier, either monofilament, multifilament or any combination thereof may be used. The braid pattern may, for example, employ strands running parallel to the major axis of the tube. It should be understood that any suitable form of textile material or combination of forms such as, but not limited to, woven materials, non-woven materials, knitted materials and/or braided materials may be used to create a suitable middle layer 304. For example, it is contemplated that a suitable middle layer 304 may be created using a textile other than a braid alone or in combination with a braid.

Middle layer 304 need not be in the form of a continuous tube and need not be a continuous layer throughout the entire length of the balloon 114. For example, narrow strips of suitable textiles may be arranged to create a middle layer 304. Alternatively, strips of textiles may be arranged helically to create a middle layer 304. Still further, balloon 114 may comprise a middle layer 304 in only a portion or portions of the balloon length. Also, balloon 114 may comprise a middle layer 304 that varies in thickness and/or strength along the length of the balloon.

As is typical for braided tubes, braided tube 400 exhibits a relationship between its diameter and its length. In order to treat the exemplary braided tube 400 such that it may increase in diameter with substantially no change in length, braided tube 400 is preferably fitted coaxially over an approximately 1.65 mm diameter stainless steel rod. Braided tube 400 is then axially elongated such that it reduces in diameter and fits snugly onto the outer surface of the rod. Each end of braided tube 400 is then secured to the rod with wire, maintaining the axially elongated/reduced diameter condition. FIG. 4B shows an enlarged illustration of the braid pattern of braided tube 400 in the axially elongated/reduced diameter condition.

With braided tube 400 secured to the rod, thin PTFE film is helically wrapped about the outer surface of the tube to further secure the tube to the stainless steel rod. The wrapping of the PTFE film may be completed manually, with minimal tension. The wires at each end of braided tube 400 are then removed, marks may be placed at approximately 10 mm intervals along the entire length of the helically wrapped tube, and the tube/rod assembly can be placed into an air convection oven set at approximately 70° C. for a minimum of 15 minutes.

After the passing of a minimum of 15 minutes the tube/rod assembly is preferably removed from the oven and, while still warm, the tube is axially compressed until the marks placed at the approximately 10 mm intervals are spaced consistently at approximately 6.5 mm intervals. The 15 minute, 70° C. parameters are chosen to facilitate the axial compression. Any suitable time and temperature combination may be utilized. During the compression, the braid pattern of the tube 400 densifies and small corrugations form along the surface of the tube. The PTFE film, however, serves to substantially maintain the reduced diameter of braided tube 400 during the axial compression inhibiting the formation of gross corrugations. With braided tube 400 axially compressed, the tube/rod assembly is preferably placed into an air convection oven set at approximately 197° C. for approximately 3.5 minutes and then removed to cool to ambient temperature. Once cool, the PTFE film is removed and braided tube 400 is carefully removed from the rod. At this point the braided tube is capable of undergoing an increase in diameter without a substantial change in length.

The 3.5 minute 197° C. treatment imparts a thermal set into braided tube 400, without substantially melting or bonding the strands of the tube, rendering the tube substantially dimensionally stable and easily handled. Any suitable time and temperature combination may be utilized. In some instances a more aggressive thermal treatment may be preferred or required such that all or portions of the material(s) used soften and mildly bond to one another. FIG. 4C shows an enlarged illustration of the compression of the braid pattern of braided tube 400.

As previously stated any suitable time/temperature combinations may be utilized in the various thermal treatment and axial compression steps described above. Additionally, any suitable means of achieving the compression of the braid pattern of braided tube 400 may be employed. For example, braided tube 400 may be placed within a glass tube having an inner diameter appropriate to cause braided tube 400 to assume an axially elongated/reduced diameter condition. A rod of appropriate material and diameter may then be fitted coaxially within braided tube 400. Preferably, the rod is slidable yet snugly fit within braided tube 400. The glass tube/rod assembly may then be suitably heated. With the glass tube/rod assembly heated, tubing of appropriate material, having an outer diameter able to be inserted within the glass tube and having an inner diameter able to accommodate the rod, may be inserted into each end of the glass tube. Preferably, the tubing is slidable within the glass tube and over the rod yet snugly fit to both, acting in a fashion similar to a piston within the glass tube. The tubing at each end of the glass tube may then be slid toward the center of the glass tube causing braided tube 400 to axially compress to the desired amount. Next, the axially compressed braided tube 400, while in the glass tube, may be suitably thermally treated, then allowed to cool and removed form the glass tube.

Regardless of the technique employed to achieve the axial compression, various forms of balloon 114 may include middle layers with any suitable amount of axial compression. For example, if a braided tube is used within a balloon the amount of axial compression desired may depend on the braid pattern of the tube. Some braid patterns may not be constant along the length of the braided tube and, as such, may require different amounts of axial compression along the length of the tube. Varying degrees of axial compression may result in varying degrees of corrugations. The formation of the corrugations may also be dependent on the technique employed to achieve the axial compression. In some forms of balloon 114 suitable axial compression may be achieved without any formation of corrugations.

It may also be desirable for balloon 114 to either shorten or lengthen as it is inflated. For example, if balloon catheter 100 is used to deploy a stent that shortens as it grows in diameter, it may be desirable for balloon 114 to shorten in unison with the stent during deployment. Conversely, in such an application of balloon catheter 100, it may be desirable for balloon 114 to slightly lengthen during inflation to counteract the shortening of the stent being deployed.

While this example utilizes a braided tube that is treated to allow the tube to experience a change in diameter with no substantial change in length, it is to be understood that the treatment need not be applied to a completed braided or otherwise suitable textile tube. For example, the individual strands utilized in the construction of the tube may be treated. Additionally, the arrangement of untreated strands with respect to one another may be such that the resulting tube or layer will experience a change in diameter with no substantial change in length in a manner that is suitable for use in balloon 114.

With the axially compressed braided tube 400 completed, one layer is fitted over the silicone tubing comprising inner layer 302. In this illustrated example, braided tube 400 is somewhat loose over inner layer 302, so the layer of braided tube 400, while over the silicone tubing comprising inner layer 302, is helically wrapped with PTFE film resulting in a more snug fit between the two. The PTFE wrapped inner layer 302 and layer of braided tube 400, while on the approximately 1.19 mm diameter rod, are placed within an air convection set at approximately 197° C. for approximately 3.5 minutes then removed and allowed to cool to ambient temperature. Once cool, the PTFE film is removed. Another layer of braided tube 400 is then placed over the first and the helical wrapping, the thermal treatment, the cooling, and the removal of the wrapping film are all repeated. Thus, 2 layers of braided tube 400 are applied to the inner layer 302.

While this example employs PTFE film to create a snug fit between inner and middle layers 302 and 304, respectively, any suitable method may be used. For example, shrink tubing of any suitable material or a heated die of appropriate dimension may be used. Depending on the material(s) used for the inner and middle layers, it may be desirable to embed at least a portion of the middle layer 304 into inner layer 302 by using any suitable means of heat and pressure.

Outer layer 306 may be next applied by covering the outer surface of the 2 layers of compressed braided tube 400 with 2 coats of a 1:1 mixture of MED-1511 Adhesive Silicone (which may be sourced from NuSil of Carpinteria, Calif.) and Heptane. The 1:1 mixture is measured by weight. In this example of balloon 114 outer layer 306 is intended to encapsulate middle layer 304 and bond to inner layer 302 thus unifying the individual layers into a composite tubular structure. During careful application of the first coat, the mixture penetrates through both layers of the treated braided tube 400 thus coming into contact with inner layer 302. Once the first coat of the mixture is applied it is allowed to cure in a high humidity environment for a minimum of 18 hours. A second coat of the same silicone/heptane mixture is then applied over the first coat and cured in the same manner as the first coat.

While the example outer layer 306 comprises a silicone mixture, which after curing results in a uniform silicone layer, any suitable material or combination of materials may be used. Such materials include but are not limited to latex, polyurethane, PEBA, and/or fluoroelastomers. Preferably, the materials that comprise layers 302 and 306 are chosen on the basis of their elastic and strength properties. In this manner, the materials are chosen such that the layer(s) may undergo the desired change in diameter during inflation without breaking and return to their original dimensions upon deflation.

Various methods or combinations of methods may be employed to create a suitable outer layer 306. For example, outer layer 306 may comprise a suitable silicone tube that may be fitted coaxially over layers 302 and 304, and that may be attached to the layers by various elastomers applied as adhesives. Conversely, outer layer 306 may not be attached, or may only be partially attached to layers 302 and/or 304. Other methods for the creation of an outer layer 306 include, but are not limited to, dipping, application by spraying, and/or molding. Some forms of balloon 114 may utilize extrusion as a method of creating outer layer 306 over layers 302 and 304. Depending on the material(s) utilized, it may be advantageous to apply outer layer 306, as a tube, over layers 302 and 304 and then bond the layers to create a unified composite tubular structure using, for example, suitable shrink tubing or an appropriately sized and heated die. It may be advantageous in some cases to extrude or otherwise mold a suitable material around a treated braided tube or other suitable middle layer 304, thus creating layers 302 and 306 with one process. Furthermore, some forms of balloon 114 may provide outer layer 306 with regions of porosity that allow the passage of fluids there through while still allowing balloon 114 to be inflated.

Once the second coat is cured, the exemplary balloon 114 is completed. This particularly described balloon 114 is produced to create a liquid tight balloon material. Further processing, however, may be completed in order to create regions of porosity within the balloon material. The processing may be completed in any suitable manner, for example, the balloon material may be treated by a laser to create holes of a controlled diameter, or holes may be created with pins. As previously mentioned, the regions of porosity may allow various therapeutic agents to be delivered to bodily conduits while allowing the balloon to inflate.

When the second coat is cured the exemplary balloon 114 is carefully removed from the approximately 1.19 mm diameter rod. To facilitate the removal of balloon 114 from the rod, small portions of each end of the balloon 114 may be cut off and the rod may be placed in a bath of isopropyl alcohol. The isopropyl alcohol penetrates between the balloon 114 and the rod thus providing lubrication during the removal process. After removal from the rod, the alcohol is allowed to evaporate from the exemplary balloon 114.

A segment of the exemplary balloon 114, approximately 30 mm long, is then cut. In order to measure the inflation characteristics (compliance) of the balloon, blunt needles having an outer diameter of approximately 1.3 mm and equipped with luer fittings are inserted into each end of the segment of exemplary balloon 114. Tuohy-Borst adapters (part MX220, manufactured by Medex Medical, Dublin, Ohio) may be used to create a watertight seal between the needles and the exemplary balloon 114. One needle is sealed with a luer cap, while the other is connected to a hand-held inflation syringe filled with water.

Prior to any inflation, the distance between the two Tuohy-Borst adapters is measured to be approximately 18.27 mm. Also, the outer diameter of the balloon is measured to be approximately 2.36 mm. The balloon is then inflated, at ambient temperature, in increments of approximately 0.1 MPa (1 atm) and the outer diameter of the balloon is measured at each increment until a pressure of approximately 0.6 MPa (6 atm) is achieved. During the inflation, the distance between the Tuohy-Borst adapters is measured to be 18.43 and 18.98 mm at approximately 0.4 and 0.6 MPa (4 and 6 atm) respectively. These data translate into a maximum change in length during inflation of 0.71 mm which, when expressed as a percentage of the balloon length prior to inflation, is approximately 4%. Once all of the measurements are taken, the exemplary balloon 114 is deflated and the outer diameter and distance between the Tuohy-Borst adapters are measured to be 2.31 and 18.27 mm respectively, indicating that the exemplary balloon exhibits an elastic response returning to nearly its original dimensions after being inflated.

The same test procedure is repeated, yielding compliance data for the exemplary balloon 114 during a second inflation. During this second inflation the distance between the Tuohy-Borst adapters is measured to be 18.58 mm at approximately 0.4 MPa (4 atm), showing a small change in length similar to that of the first inflation. All diameter and length measurements are taken with a pair of digital calipers.

With the second inflation completed, the blunt needles and Tuohy-Borst adapters are removed and barbed luer fittings (for example, part FTLL210-9 manufactured by Value Plastics Inc., Fort Collins, Colo.) are inserted into each end of the length of exemplary balloon 114. Wax-coated thread is then tied around each end, providing a watertight seal between the barbed luer fittings and the balloon. Next, one barbed luer fitting is sealed with a luer cap while the other is connected to a hand-held inflation syringe filled with water and the balloon is inflated until rupture occurs.

This exemplary balloon 114 ruptures at approximately 0.8 MPa (8 atm). When tested in the same manner, the silicone tubing comprising inner layer 302 ruptures at approximately 0.1 MPa (1 atm). Therefore, the addition of the 2 layers of treated braided tube 400 (middle layer 304) and outer layer 306 results in an approximately eight-fold increase in burst strength.

The compliance characteristics of exemplary balloon 114 are shown in FIG. 5. In this regard, the compliance signature of exemplary balloon 114 during the first inflation is clearly different from that of the balloon during the second inflation. During the first inflation, most of the diameter growth of exemplary balloon 114 occurs between approximately 0.3 and 0.6 MPa (3 and 6 atm), while very little diameter growth occurs between approximately 0 and 0.3 MPa (0 and 3 atm). During the second inflation, most of the diameter growth of the exemplary balloon occurs between approximately 0 and 0.2 MPa (0 and 2 atm), with a significant change in the slope of the compliance curve occurring at approximately 0.2 MPa (2 atm). The difference in the two compliance signatures is an aspect of balloon 114 that may be tailored and employed to enhance usage of balloon catheter 100.

For example, referring to FIGS. 1 and 6A, the distal portion of balloon catheter 100 may be placed within inflation mold 602 with balloon 114 centered lengthwise with respect to the large diameter cavity within the mold. The mold 602 may be sized such that the large cavity is approximately half of the length of balloon 114 and of approximately the nominal inflated diameter of the balloon. Balloon 114 may then be inflated within the mold causing the balloon material to adopt the shape of the mold. In this manner, the center region of the balloon 114, having been inflated to its nominal diameter, will have a compliance signature corresponding to the second inflation curve as shown in FIG. 5. The end regions of the balloon, not having been inflated to a substantially larger diameter, will have a compliance signature corresponding to the curve of the first inflation. Balloon 114, after such a treatment, essentially exhibits regions of varying compliance.

Balloon 114, treated by inflation within mold 602, may provide enhanced control during an angioplasty procedure. For example, if the balloon catheter 100 is being used to remodel a stenotic lesion of relatively short length, balloon 114 may be placed, centered lengthwise with respect to the lesion. Upon inflation, the center of balloon 114 inflates first, coming into contact with the stenotic tissue and initiating the angioplasty process. The end regions of balloon 114, changing in diameter at a lesser rate, remain smaller than the center and do not contribute to the remodeling of the stenotic tissue. Eventually, with increasing pressure all of the regions of balloon 114 reach approximately the same diameter.

An inflation mold 608 wherein one half of the mold is of a larger inner diameter than the other half is further illustrated in FIG. 6B. The larger diameter half of inflation mold 608 may be of approximately the nominal inflated diameter of the balloon 114. Such an inflation mold, employed in a fashion similar to that described above, may be utilized to create a balloon 114 that inflates at a faster rate at one end. Such a balloon 114 may enhance the angioplasty process by not only pressurizing and expanding diseased blood vessels, but by also redistributing the diseased tissue in a predetermined lengthwise manner. Such a balloon 114 may be utilized, for example, in situations wherein an occlusive lesion is located very close to the origin of a side-branch vessel and redistribution of the diseased tissue away from the side-branch vessel origin is highly advantageous.

While inflation molds 602 and 608 each have a region that allows a balloon 114 to inflate to approximately its fully inflated diameter, inflation molds may be created that allow the balloon to inflate only partially. For example, a balloon with a fully inflated diameter of approximately 6 mm may only be allowed to inflate to approximately 4 mm within a mold. Thus, various inflation molds may be created to achieve various results. Any suitable inflation mold may be used to create any balloon embodiment having regions of distinct compliance characteristics. Conversely, it may be desirable in some instances to create a balloon that has a single compliance characteristic throughout its entire length. This may be accomplished through the use of an inflation mold having a constant inner diameter. It is to be understood that an inflation mold is not required when an inflation process is used to affect the compliance characteristics of the balloon.

While any suitable inflation mold geometry may be employed to create any desired form of balloon, certain inflation molds may be used more commonly than others. In order to facilitate routine usage of inflation molds to customize the compliance characteristics of various balloon 114, it may be desirable or otherwise advantageous to provide a set or a kit of inflation molds having commonly used geometries to physicians. In this manner, a balloon provided by a manufacturer may, by virtue of being customized, be transformed into various embodiments each particularly treated to meet a specific need. It may be desirable to combine the aspect of treating a balloon by inflating it within a mold, with varying the materials or the amount of materials utilized along the balloon length. Such combinations may be utilized to create a balloon 114 with dramatically different regions of compliance. For example, a balloon 114 wherein middle layer 304 is twice as thick at one half of the balloon length may be created. Each half of such a balloon 114 would have distinct compliance characteristics than the other, the half with the thinner middle layer 304 being the more compliant of the two. This balloon 114 may then be situated within inflation mold 608 such that the half of the balloon with the thicker region of middle layer 304 is located within the region of smaller diameter within mold 608 and suitably inflated within the mold. In such a manner, two of the described aspects may be combined to create various balloons with regions of different compliance. Balloons with regions of different compliance that include regions of porosity for the delivery of therapeutic agents may also be created.

Additionally, the aspect of treating a balloon by inflating it within a mold may be combined with utilizing a braid or other textile having any suitable geometry such as, but not limited to, tapers or teardrop shapes to create balloons that are suited to specific bodily conduit geometries. Such balloon embodiments may also include regions of porosity for the delivery of therapeutic agents.

It is to be understood that the aspects of compliance and balloon shape may be varied independently or in combination. For example, a balloon designed to be of a constant outer diameter may be treated to have variable compliance (e.g., by usage of an inflation mold) such that prior to being fully inflated the balloon exhibits a tapered shape. On the other hand, by combining the aspects of compliance and balloon shape, a balloon designed to have a tapered shape may be treated by using an inflation mold to assume a constant diameter along its length prior to being fully inflated.

As previously mentioned, middle layer 304 need not be in the form of a continuous tube, and need not be a continuous layer throughout balloon 114. Any suitable number of layers may be employed to create various embodiments of balloon 114. In various adaptations, any number of layers with suitable attributes may be advantageously arranged so as to cooperate with each other during inflation to form a balloon with a predetermined shape.

To produce an example balloon 114 having a predetermined shape, an approximately 100 mm length of silicone tubing may be fitted coaxially onto an approximately 0.50 mm diameter stainless steel rod approximately 317 mm in length. Isopropyl alcohol may be used as a lubricant to facilitate the fitting. An example silicone tubing, comprising inner layer 302, has a nominal inner diameter of 0.48 mm, a nominal wall thickness of 0.10 mm, and is manufactured by Specialty Silicone Fabricators located in Paso Robles, Calif.

An approximately 152 mm length of stainless steel hypodermic tubing, having an inner diameter of 0.63 mm and an outer diameter of 0.82 mm may be fitted coaxially over the 0.50 mm diameter stainless steel rod and carefully inserted approximately 30 mm into the silicone tubing comprising inner layer 302. Preferably, the hypodermic tubing is situated over the rod such that the end not covered by the silicone tubing is approximately 60 mm away from the corresponding end of the rod. Isopropyl alcohol may be used as a lubricant to facilitate the insertion of the hypodermic tubing within the silicone tubing. With the silicone tubing fitted over the stainless steel rod and hypodermic tubing, the entire assembly is preferably placed within an air convection oven set at 70° C. for approximately 10 minutes to evaporate any residual alcohol.

In this arrangement, the stainless steel rod and hypodermic tubing comprise inner catheter member 108 and outer catheter member 110 respectively, with the lumen of the hypodermic tubing comprising lumen 212. In this example, because inner catheter member 108 is comprised of a rod as opposed to a tube, as depicted by the exemplary catheter shown in FIG. 2, a lumen 210, a step 204, or markers 206 and 208 need not be present. Similarly, because outer catheter member 110 is comprised of hypodermic tubing, a 202 need not be present.

In keeping with this example, the middle layer 304 of balloon 114 may comprise two distinct layers of treated braided tube 400, as illustrated in FIG. 7. An exemplary first braided tube 400a has an approximate relaxed inner diameter of 5 mm created from 36 individual strands of polyester multifilament yarn. Eighteen of the 36 strands are 44 denier while the other 18 are 20 denier. The braid density of the tube is approximately 15.4 pixels per centimeter (39 pixels per inch). Such a tube is manufactured by Secant Medical, L.L.C. of Perkasie, Pa.

As previously discussed, braided tube 400 exhibits a relationship between its diameter and its length. In this example, the first braided tube 400a is treated to increase in diameter with no substantial change in length by preferably coaxially fitting the tube over an approximately 0.65 mm diameter stainless steel rod. The first braided tube 400a is then axially elongated such that it reduces in diameter and fits snugly onto the outer surface of the rod. Each end of the first braided tube 400a is then secured to the rod using small hemostats, maintaining the axially elongated/reduced diameter condition. FIG. 4B shows an enlarged illustration of the braid pattern that would result from the first braided tube 400a being in the axially elongated/reduced diameter condition.

With the first braided tube 400a secured to the rod, thin PTFE film is helically wrapped about the outer surface of the tube to further secure the tube to the stainless steel rod. The wrapping of the PTFE film may be completed manually, with minimal tension. The hemostats at each end of the first braided tube 400a are then removed. Marks are placed at approximately 10 mm intervals along the entire length of the helically wrapped tube, and the tube/rod assembly may be placed into an air convection oven set at approximately 70° C. for a minimum of 15 minutes.

After the passing of a minimum of 15 minutes the tube/rod assembly is removed from the oven and, while still warm, the tube is axially compressed until the marks placed at the approximately 10 mm intervals are spaced consistently at approximately 7.5 mm intervals. With the first braided tube 400a axially compressed, the tube/rod assembly is preferably placed into an air convection oven set at approximately 197° C. for approximately 5.0 minutes and then removed to cool to ambient temperature. Once cool, the PTFE film is removed and the first braided tube 400a is preferably carefully removed from the rod. At this point the first braided tube 400a is capable of undergoing an increase in diameter without a substantial change in length.

The 5.0 minute 197° C. treatment imparts a thermal set into the first braided tube 400a, without substantially melting or bonding the strands of the tube, rendering the tube substantially dimensionally stable and easily handled. Any suitable time and temperature combination may be utilized. FIG. 4C shows an enlarged illustration of the compression of the braid pattern of an exemplary first braided tube 400a.

With the first braided tube 400a treated to increase in diameter without a substantial change in length, a 60 mm length of the tube is cut and carefully fitted coaxially over the silicone tubing comprising inner layer 302 such that one end of the treated braided tube is coincident with the end of the silicone tube over the hypodermic tubing. Isopropyl alcohol may be used as a lubricant to facilitate the fitting.

The second braided tube 400b is prepared for use in a balloon 114. An exemplary second braided tube 400b has an approximate relaxed inner diameter of 3 mm and is created from 24 individual strands of polyester multifilament yarn. Twelve of the 24 strands are 44 denier while the other 12 are 20 denier. The braid density of the tube is approximately 17.7 pixels per centimeter (45 pixels per inch).

A 90 mm length of the second braided tube 400b is fitted coaxially onto a 3.18 mm diameter PTFE rod or more preferably a 3.0 mm diameter PTFE rod. The fitting is preferably performed very carefully, without disturbing the braid pattern of the tube. While on the PTFE rod, a 2.5 mm diameter dermal biopsy punch manufactured by Miltex, Inc. of Bethpage N.Y. may be used to create a circular hole at the midpoint of second braided tube 400b. In this case, the PTFE rod is well suited to support the braided tube during the creation of the hole. The rod is stiff enough to provide dimensional stability, yet the PTFE material is soft enough to allow the biopsy punch to penetrate into it, resulting in a clean cut with minimal fraying of the braided tube. Any suitable method may be employed to create any suitable size or shape hole through the second braided tube 400b. For example, the hole may be created by laser cutting or a hole may be created by locally distorting the pattern of a braided or other suitable textile tube. Suitable holes may be created in various shapes such as, but not limited to, circles, ellipses, squares, rectangles, triangles and various polygons. As will be appreciated, the original shape of a hole may change as a result of processing and/or a change in diameter of the balloon, e.g., an elliptical hole may assume a circular shape upon the balloon being expanded.

With the 2.5 mm hole created in the second braided tube 400b, the tube is removed from the PTFE rod and an indelible ink marker may be used to outline the perimeter of the hole for ease of identification in future processing. Next, the second braided tube 400b is treated to be able to increase in diameter with no substantial change in length. The same process used to treat the 5 mm first braided tube 400a described above may be used to treat this braided tube, except that in this case the tube is fitted onto a 0.86 mm stainless steel rod and is axially compressed until the marks spaced at 10 mm are spaced consistently at 6.5 mm. The treatment is preferably executed carefully, with particular attention paid to the pattern of the braided tube in the vicinity of the hole. Once the second braided tube 400b is treated, a 60 mm length is cut with the hole created by the biopsy punch positioned at the midpoint.

Next, PTFE film is wrapped around one end of the 5 mm first braided tube 400a fitted coaxially over the silicone tube comprising inner layer 302. The wrapping is initiated at the end of the braided tube that is over the 0.50 mm diameter stainless steel rod and only covers 3 to 6 mm of the braided tube. This is done to minimize the diameter of the end and stabilize the first braided tube 400a during the next step. With the end of the 5 mm first braided tube 400a wrapped, an 80 mm length of 1.15 mm inner diameter polyester shrink tubing (e.g., part 045050CST, manufactured by Advanced Polymers, Inc. of Salem N.H.) is fitted coaxially over the 5 mm braided tube. Prior to being fit over the first braided tube 400a, a longitudinal cut approximately 6 mm long is made through both walls of one end of the shrink tube. The fitting is preferably done carefully without distorting the pattern of the first braided tube 400a. Isopropyl alcohol may be used as a lubricant to facilitate the fitting. Preferably, any residual alcohol is allowed to evaporate at ambient temperature before proceeding to the next steps.

The entire assembly is then placed in an air convection oven set at 197° C. for 5.0 minutes, then removed and allowed to cool to ambient temperature. The 5.0 minute thermal treatment causes the shrink tubing to reduce in diameter while simultaneously imparting a thermal set into the first braided tube 400a, reducing the diameter of the braided tube and stabilizing the tube dimensionally for the subsequent process steps. Any suitable time and temperature combination may be utilized. Once cool, a razor blade may be used to lightly score the shrink tubing along its entire length. This procedure is again preferably performed very carefully, ensuring that the razor blade does not cut the underlying braided tube. With the shrink tubing scored, it may be carefully peeled away using the tabs created from the 6 mm longitudinal cut.

The 60 mm length of treated 3 mm braided tube 400b may then be fitted coaxially over the treated 5 mm braided tube 400a such that the ends of the tubes are coincident. Again, the fitting is preferably done carefully without distorting the pattern of the treated braided tubes. Isopropyl alcohol may be used as a lubricant to facilitate the fitting.

Using the same technique that is used on the 5 mm braided tube 400a, one end of the 3 mm braided tube 400b is wrapped with PTFE film. In the same fashion as described above, polyester shrink tubing may be utilized to reduce the diameter and thermally set both the 5.0 and the 3.0 mm braided tubes now over the silicone tubing comprising inner layer 302, except in this case the inner diameter of the shrink tubing is 1.58 mm (e.g., part number 062050CST, manufactured by Advanced Polymers, Inc. of Salem N.H.).

With the 1.58 mm inner diameter shrink tubing removed, both distinct, treated braided tube 400 layers, creating an exemplary middle layer 304, are situated coaxially over inner layer 302. Next, an 80 mm length of silicone tubing comprising outer layer 306 is fitted coaxially over inner layer 302 and middle layer 304. The fitting is initiated at the wrapped ends of the braided tubes 400 comprising the middle layer 304. The silicone tubing comprising outer layer 306 preferably has a nominal inner diameter of 1.10 mm, a nominal wall thickness of 0.10 mm and is manufactured by Specialty Silicone Fabricators located in Paso Robles, Calif. Isopropyl alcohol may be used as a lubricant to facilitate the fitting. Once the silicone tubing comprising outer layer 306 is fitted over inner and middle layers 302 and 304, respectively, the entire assembly is preferably placed within an air convection oven set at 70° C. for approximately 10 minutes to evaporate any residual alcohol. After the residual alcohol is evaporated, a razor blade may be used to trim away any excess silicone tubing extending beyond the length of middle layer 304, leaving a 60 mm long embodiment of balloon 114 situated over the stainless steel rod and hypodermic tubing comprising inner and outer catheter members 108 and 110 respectively. Note that in this exemplary balloon 114 layers 302, 304 and 306 are preferably not attached to each other.

In order to inflate this exemplary balloon 114, an apparatus to introduce an inflation fluid such as water into lumen 212 is created. A double female luer lock adapter (e.g., part MX494, manufactured by Medex Medical of Dublin, Ohio) is connected to a Y connector with a male rotating luer and 2 female luers such as, for example, part 83016 manufactured by Qosina of Edgewood N.Y. Tuohy-Borst adapters may then be connected to the open luer of the double female luer lock adapter and to the luer of the Y connector that is in line with the double female luer lock adapter. This assembly is then fitted onto the balloon assembly such that one Tuohy-Borst adapter creates a seal around the hypodermic tubing, while the other creates a seal around the stainless steel rod extending beyond the hypodermic tubing. In this arrangement, the assembly functions as a proximal adapter 102 (FIG. 1), with the open female luer extending from the side of the Y connector comprising balloon port 106.

Next, a Tuohy-Borst adapter is placed over proximal end of the exemplary balloon, creating a seal between the balloon and the hypodermic tubing, and a 40 mm long, 2.0 mm inner diameter glass tube is placed over the balloon. Another Tuohy-Borst adapter is then placed over the distal end of the balloon, creating a seal between the balloon and the 0.50 diameter stainless steel rod.

A hand-held inflation syringe filled with water is connected to the female luer comprising balloon port 106, and the balloon is inflated, at ambient temperature, to between 0.2 and 0.3 MPa (2 and 3 atm). Under this inflation pressure, the outer surface of the exemplary balloon comes substantially into contact with the inner surface of the 2.0 mm inner diameter glass tube. The balloon is then deflated, and the Tuohy-Borst adapter at the distal end of the balloon and the 2.0 mm inner diameter glass tube are removed. A 40 mm long, 3.0 mm inner diameter glass tube is then placed over the exemplary balloon and the Tuohy-Borst adapter is replaced. The balloon is inflated, again at ambient temperature, to between 0.3 and 0.4 MPa (3 and 4 atm), causing the outer surface of the balloon to substantially contact the inner surface of the glass tube. In this fashion, the 2.0 and 3.0 mm glass tubes (e.g., manufactured by Farlows Scientific Glassblowing, Inc. of Grass Valley, Calif.) are serving as inflation molds of a constant diameter. The balloon is then deflated, the 3.0 mm glass tube is removed, and the Tuohy-Borst adapters are repositioned such that each is approximately 10 mm away from the region of the hole created by the biopsy punch.

Because the region of the exemplary balloon 114 in the vicinity of the hole created by the biopsy punch is intended to inflate to a different dimension than the rest of the balloon, forming a specific shape, this exemplary balloon 114 is preferably initially inflated within the 2.0 and 3.0 mm inner diameter molds to allow, in subsequent inflations, the balloon to inflate in a substantially uniform fashion prior to the region of the hole inflating beyond the diameter/shape of the remainder of the balloon. Thus, the compliance characteristics of the balloon are tailored such that the balloon inflates in a uniform manner prior to the region of the hole assuming its intended shape.

Next, the balloon is inflated, at ambient temperature, to approximately 0.4 MPa (4 atm) with no mold present. At this pressure the balloon assumes the intended shape with the region in the vicinity of the hole assuming a substantially elliptical geometry, protruding from the remainder of the balloon. When the described balloon is measured using digital calipers, the dimension of the elliptical protrusion along the major axis of the balloon is approximately 7 mm and the dimension along the minor axis of the balloon is approximately 3.5 mm. The protrusion measures approximately 3 mm in height.

This exemplary balloon 114 may be utilized, for example, in situations wherein an occlusive lesion is located at the origin of a side-branch vessel and it is advantageous for the balloon to assume the geometry of the side-branch vessel origin. Additionally, this exemplary balloon 114 may have utility in deploying stents having geometries intended for usage at the origins of side-branch vessels.

While this exemplary balloon 114 is treated within an inflation mold of constant diameter, it may be advantageous to treat the exemplary balloon 114 in an inflation mold that mimics the predetermined shape of the balloon. For example, FIG. 6C shows an inflation mold 612 that simulates the geometry of the origin of a side-branch vessel. Exemplary inflation mold 612 is configured to allow the side protrusion to inflate, while maintaining the rest of the balloon below the fully inflated diameter. Such an inflation mold 612 may be utilized to create forms of balloon 114 that have side protrusions that inflate at a faster rate than the rest of the balloon. Such a balloon 114 may be utilized, for example, in situations where it is advantageous for the balloon to come into contact with the side-branch vessel origin first and redistribute the occlusive tissue such that flow into the side-branch vessel is restored. Such a balloon 114 may also have utility in enhancing the deployment of stents intended for usage at the origins of side-branch vessels.

For further illustration, an exemplary balloon 114 with a substantially circular side protrusion is produced. The exemplary balloon 114 may be created following the same procedure as the previous example, except that rather than forming a circular hole through 3 mm braided tube 400*b*, an elliptical hole is formed. In this example, an elliptical hole is laser cut through 3 mm braided tube 400*b* by a small scale computer controlled laser at the facilities of Secant Medical, L.L.C. located in Perkasie, Pa. The control parameters are set to produce an elliptical hole having a 1.5 mm long major axis oriented along the transverse axis of the braided tube 400*b*, and a 0.75 mm long minor axis oriented along the major or longitudinal axis of braided tube 400*b*. Additionally, in this example the steps of coaxially fitting shrink tubing and thermally treating braided tubes 400*a* and 400*b* over inner layer 302 are omitted. Rather, the braided tubes 400 and the silicone tubing comprising outer layer 306 are coaxially arranged as previously described without the added thermal treatments. It is to be noted that the lack of the additional thermal treatments does make the coaxial fitting of the layers more difficult, resulting in a small amount of disruption and elongation to the patterns of the treated tubes 400*a* and 400*b*.

Once completed, the exemplary balloon 114 is inflated within the 2.0 and 3.0 mm molds as described above. When inflated to approximately 0.4 MPa (4 atm) with no mold present the balloon assumes its intended shape with the region in the vicinity of the hole assuming a substantially circular geometry, protruding from the remainder of the balloon. When measured using digital calipers, the substantially circular protrusion has a diameter of approximately 2.4 mm and a height of approximately 0.7 mm.

In certain situations, an embodiment of balloon 114 wherein the side protrusion extends beyond the remainder of the balloon a greater amount may be desirable. Such an embodiment of balloon 114 may be produced by various suitable methods. For example in order to provide more material to protrude through the exemplary hole in braided tube 400b as described in the previous example, the region of braided tube 400a which is beneath the exemplary hole may be axially compressed such that the marks spaced originally at 10 mm are spaced, for example, at 5 mm (as opposed to 7.5 mm, as previously described).

Any suitable method of attachment may be employed to connect the various forms of balloon 114 to the various catheter member(s) in order to create various balloon catheters 100. For example, a balloon 114 may be attached to steps 202 and 204 (see FIG. 2) with various adhesives or combinations of adhesives such as, but not limited to, cyanoacrylates, or adhesives that are cured via ultra-violet light. In some embodiments of balloon catheter 100, balloon 114 may be thermally bonded to the catheter member(s).

Various techniques may also be employed to enhance the connection between balloon 114 and the catheter member(s). For example, reinforcing bands made in any suitable configuration of any suitable material may be placed around balloon 114 coincident to the points at which the balloon is attached to the catheter member(s). Alternatively, the regions of attachment may be wrapped by reinforcing filaments of any suitable material. Thin films may also be utilized to this end.

Some forms of balloon catheter 100 may take advantage of multi-layer forms of balloon 114 by integrating any number of any of the balloon layers into the catheter member(s). For example, in the balloon 114 shown by way of example in FIG. 3, middle layer 304 may extend beyond the edges of layers 302 and 306. The portions of middle layer 304 extending beyond the other balloon layers may be integrated into inner and outer catheter members 108 and 110 respectively or into any other suitable catheter member(s).

By way of further example, a desired length of inner layer 302 may be attached by any suitable method to steps 202 and 204, or to any suitable element of the catheter member(s). Middle layer 304, suitably longer than inner layer 302 may then be fitted coaxially over inner layer 302. Additional catheter member material may then be applied over the regions of middle layer 304 that extend beyond the edges of inner layer 302. The additional catheter material may be applied by any suitable method. For example, the additional material may be injection molded over the regions of middle layer 304 that extend beyond the edges of inner layer 302. Alternatively, thin tubing may be applied over the regions of middle layer 304 that extend beyond the edges of inner layer 302. The thin tubing may be attached to the middle layer 304 as well as the catheter member(s) by any suitable method such as the use of an adhesive or various thermal bonding techniques. Various forms of distal tip 116 may be formed in such a manner. With middle layer 304 suitably integrated into the catheter member(s), outer layer 306 may be applied by any suitable method such as, but not limited to, application in the form of a mixture (as described above), or alternatively outer layer 306 may comprise a tube similar to inner layer 302. Regardless of embodiment, outer layer 306 may extend onto the catheter member(s) if desired. Integration of one or more layers of balloon 114 into the catheter member(s) may be advantageous by providing a very sleek profile to the distal region of balloon catheter 100 as well as a very reliable and strong connection between balloon 114 and the catheter member(s).

The present invention has been described above with reference to various exemplary embodiments. However, changes and modifications may be made to the described, exemplary embodiments without departing from the scope of the present invention. For example various forms of the distal portion of balloon catheter 100, particularly with regard to the arrangement of catheter members 108 and 110 and balloon 114 may be provided. Additionally, various changes in the configuration and the materials of balloon 114 may be provided. These and other changes or modifications are intended to be included within the scope of the present invention as set forth in the appended claims.

What is claimed is:

1. A balloon for use in a catheter, comprising:
multiple layers of material disposed in cooperative relationship such that the balloon achieves a predefined geometry when inflated wherein at least one of the multiple layers of material is formed using a textile material and wherein the formed at least one of the multiple layers of textile material is thermally and physically treated prior to the multiple layers being disposed in cooperative relationship such that, when the multiple layers of material are disposed in cooperative relationship, the multiple layers of material will experience a change in diameter without experiencing unfolding while remaining substantially the same length without aid from a mechanical device when inflated.

2. The balloon as recited in claim 1, wherein the formed at least one of the multiple layers of textile material is physically treated by being at least axially compressed.

3. The balloon as recited in claim 2, wherein the textile material comprises a braided textile material.

4. The balloon as recited in claim 1, wherein compliance characteristics of the multiple layers of material are independent of the predefined geometry.

5. The balloon as recited in claim 1, wherein the multiple layers disposed in cooperative relationship comprise a first layer of material and a second layer of material wherein the second layer is disposed over the first layer and wherein the second layer has an opening through which a portion of the first layer inflates to achieve the predefined geometry.

6. The balloon as recited in claim 5, wherein the second layer of material is formed using the textile material.

7. The balloon as recited in claim 6, wherein the textile material comprises a polyester multifilament yarn.

8. The balloon as recited in claim 5, wherein the textile material comprises a braided textile material.

9. The balloon as recited in claim 8, wherein the opening is formed by locally distorting a pattern of the braided textile material.

10. The balloon as recited in claim 5, wherein second layer of material is formed using the textile material and wherein the textile material is selected from a group consisting of polyester, nylon, polyethylene, carbon, kevlar, PEBA, and PTFE.

11. The balloon as recited in claim 5, wherein the multiple layers of material disposed in cooperative relationship further comprises a third layer of material disposed in cooperative relation to the first layer of material and the second layer of material.

12. The balloon as recited in claim 11, wherein the third layer of material is formed using the textile material and wherein the textile material is selected from a group consisting of silicone, latex, polyurethane, PBA, and fluorelastomers.

13. The balloon as recited in claim 11, wherein the third layer of material comprises a porous material.

14. The balloon as recited in claim 11, wherein the third layer of material comprises a liquid tight material.

15. The balloon as recited in claim 11, wherein the third layer of material comprises an elastomer.

16. The balloon as recited in claim 11, wherein the third layer of material at least partially overlays the second layer of material.

17. The balloon as recited in claim 11, further comprising a fourth layer of material disposed to the interior of the first layer of material.

18. The balloon as recited in claim 17, wherein the fourth layer of material is formed using the textile material and wherein the textile material is from a group consisting of silicone, latex, polyurethane, PBA, and fluorelastomers.

19. The balloon as recited in claim 5, wherein the first layer of material and the second layer of material cooperate to provide the balloon with varying compliance characteristics over its length.

20. The balloon as recited in claim 19, wherein the compliance characteristics are independent of the predefined geometry.

21. The balloon as recited in claim 5, wherein the balloon in the vicinity of the opening is adapted to inflate to a different dimension relative to the remainder of the balloon.

22. The balloon as recited in claim 21, wherein the first layer of material is axially compressed in the vicinity of the opening to allow more material to protrude through the opening when the balloon is inflated.

23. The balloon as recited in claim 5, wherein the shape of the opening determines the predefined geometry of the inflated balloon.

24. The balloon as recited in claim 23, wherein the opening is generally circular when formed.

25. The balloon as recited in claim 23, wherein the opening is generally elliptical when formed.

26. The balloon catheter as recited in claim 1, wherein the multiple layers of material comprise a first layer of material and a second layer of material wherein the second layer of material is disposed over the first layer of material and wherein the second layer of material has an opening through which a portion of the first layer of material is intended to inflate to achieve the predefined geometry.

27. The balloon catheter as recited in claim 26, wherein the second layer of material is formed using the textile material.

28. The balloon catheter as recited in claim 26, wherein the textile material comprises a polyester multifilament yarn.

29. The balloon catheter as recited in claim 26, wherein the textile material comprises a braided textile material.

30. The balloon catheter as recited in claim 29, wherein the opening is formed by locally distorting a pattern of the braided textile material.

31. The balloon catheter as recited in claim 26, wherein the second layer of material is formed using the textile material and wherein the textile a material is selected from a group consisting of polyester, nylon, polyethylene, carbon, kevlar, PEBA, and PTFE.

32. The balloon catheter as recited in claim 26, wherein the multiple layers of material further comprises a third layer material disposed in cooperative relation to the first layer of material and the second layer of material.

33. The balloon catheter as recited in claim 32, wherein the third layer of material is formed using the textile material and wherein the textile material is selected from a group consisting of silicone, latex, polyurethane, PBA, and fluorelastomers.

34. The balloon catheter as recited in claim 32, wherein the third layer of material comprises a porous material.

35. The balloon catheter as recited in claim 32, wherein the third layer of material comprises a liquid tight material.

36. The balloon catheter as recited in claim 32, wherein the third layer of material comprises an elastomer.

37. The balloon catheter as recited in claim 32, wherein the third layer of material at least partially overlays the second layer of material.

38. The balloon catheter as recited in claim 32, further comprising a fourth layer of material disposed to the interior of the first layer of material.

39. The balloon catheter as recited in claim 38, wherein the fourth layer of material is comprised of a material selected from a group consisting of silicone, latex, polyurethane, PBA, and fluorelastomers.

40. The balloon catheter as recited in claim 26, wherein the first layer of material and the second layer of material cooperate to provide the balloon with varying compliance characteristics over its length.

41. The balloon catheter as recited in claim 40, wherein the compliance characteristics are independent of the predefined geometry.

42. The balloon catheter as recited in claim 26, wherein the balloon in the vicinity of the opening inflates to a different dimension relative to the remainder of the balloon.

43. The balloon catheter as recited in claim 42, wherein the first layer of material is axially compressed in the vicinity of the opening to allow more material to protrude through the opening when the balloon is inflated.

44. The balloon catheter as recited in claim 26, wherein the shape of the opening determines the predefined geometry of the inflated balloon.

45. The balloon catheter as recited in claim 44, wherein the opening is generally circular when formed.

46. The balloon catheter as recited in claim 44, wherein the opening is generally elliptical when formed.

47. The balloon catheter as recited in claim 26, wherein the balloon has compliance characteristics such that the balloon inflates in a substantially uniform manner prior to the balloon in the vicinity of the opening assuming its intended geometry.

48. The balloon as recited in claim 1, wherein the multiple layers of material include regions of porosity for the delivery of therapeutic agents.

49. A method of making a balloon for use in a catheter, comprising:
arranging multiple layers of material in a cooperative relationship that allows the balloon to achieve a predefined geometry when inflated wherein at least one of the multiple layers of material is formed using a textile material and wherein the formed at least one of the multiple layers of textile material is thermally and physically treated prior to the multiple layers of material being arranged in the cooperative relationship such that, when the multiple layers of material are arranged in the cooperative relationship, the multiple layers of material will experience a change in diameter without experiencing unfolding while remaining substantially the same length without aid from a mechanical device when inflated.

50. The method as recited in claim 49, wherein the formed at least one of the multiple layers of textile material is physically treated by being at least being axially compressed.

51. The method as recited in claim 50, wherein the textile material is a braided textile material.

52. The method as recited in claim 49, wherein compliance characteristics of the multiple layers of material are independent of the predefined geometry.

53. The method as recited in claim 49, wherein the multiple layers of material comprise a first layer of material and a second layer of material wherein the second layer of material is disposed over the first layer of material, and wherein the second layer of material has an opening through which a portion of the first layer of material inflates to achieve the predefined geometry.

54. The method as recited in claim 53, wherein the second layer of material is formed using the textile material.

55. The method as recited in claim 54, wherein the textile material comprises a polyester multifilament yarn.

56. The method as recited in claim 53, wherein the textile material comprises a braided textile material.

57. The method as recited in claim 56, wherein the opening is formed by locally distorting a pattern of the braided textile material.

58. The method as recited in claim 53, wherein the textile material is selected from a group consisting of polyester, nylon, polyethylene, carbon, kevlar, PEBA, and PTFE.

59. The method as recited in claim 53, wherein the multiple layers of material further comprises a third layer of material disposed in cooperative relation to the first layer of material and the second layer of material.

60. The method as recited in claim 59, wherein the third layer of material is formed using the textile material and wherein the textile material is selected from a group consisting of silicone, latex, polyurethane, PBA, and fluorelastomers.

61. The method as recited in claim 59, wherein the third layer of material comprises a porous material.

62. The method as recited in claim 59, wherein the third layer of material comprises a liquid tight material.

63. The method as recited in claim 59, wherein the third layer of material comprises an elastomer.

64. The method as recited in claim 59, wherein the third layer of material at least partially overlays the second layer of material.

65. The method as recited in claim 59, further comprising a fourth layer of material disposed to the interior of the first layer of material.

66. The method as recited in claim 65, wherein the fourth layer of material is comprised of a material selected from a group consisting of silicone, latex, polyurethane, PBA, and fluorelastomers.

67. The method as recited in claim 53, wherein the first layer of material and the second layer of material cooperate to provide the balloon with varying compliance characteristics over its length.

68. The method as recited in claim 67, wherein the compliance characteristics are independent of the predefined geometry.

69. The method as recited in claim 53, wherein the balloon in the vicinity of the opening inflates to a different dimension relative to the remainder of the balloon.

70. The method as recited in claim 69, comprising axially compressing the first layer of material in the vicinity of the opening to allow more material to protrude through the opening when the balloon is inflated.

71. The method as recited in claim 53, wherein the shape of the opening determines the predefined geometry of the inflated balloon.

72. The method as recited in claim 71, wherein the opening is generally circular when formed.

73. The method as recited in claim 71, wherein the opening is generally elliptical when formed.

74. The method as recited in claim 53, wherein the opening is provided to the second layer of material prior to the second layer of material being disposed over the first layer.

75. The method as recited in claim 49, further comprising using an inflation process to vary compliance characteristics of the balloon.

76. The method as recited in claim 49, comprising placing the formed at least one of the multiple layers of textile material on a rod and thermally heating the formed at least one of the multiple layers of textile material on the rod in a convection oven for a period of time.

77. The method as recited in claim 76, comprising removing the formed at least one of the multiple layers of textile material placed on the rod from the convection oven and physically treating the heated, formed at least one of the multiple layers of textile material by axially compressing the heated, formed at least one of the multiple layers of textile material on the rod.

78. A balloon for use in a catheter, comprising:
a first layer of material which experiences a change in diameter while remaining substantially the same length when inflated; and
a second layer of material which experiences a change in diameter while remaining substantially the same length when inflated;
wherein the second layer is disposed over the first layer and wherein the second layer cooperates with the first layer to allow the balloon to achieve a protrusion which assumes a geometry of a side-branch vessel opening when inflated.

79. The balloon as recited in claim 78, wherein at least one of the first layer of material and second layer of material comprises a textile.

80. The balloon as recited in claim 78, wherein at least one of the first layer of material and second layer of material comprises a polyester multifilament yarn.

81. The balloon as recited in claim 78, wherein at least one of the first layer of material and second layer of material comprises a braided material.

82. The balloon as recited in claim 78, wherein the balloon is treated in an inflation mold that simulates the geometry of the side-branch vessel opening.

83. The balloon as recited in claim 78, wherein the protrusion inflates at a faster rate relative to the remainder of the balloon.

84. The balloon as recited in claim 78, wherein the balloon inflates at a substantially uniform rate prior to the protrusion inflating.

85. The balloon as recited in claim 78, wherein the second layer of material has an opening through which the first layer of material inflates to provide the geometry of the side branch vessel opening.

86. The balloon as recited in claim 85, wherein the opening is generally circular when formed.

87. The balloon as recited in claim 85, wherein the opening is generally elliptical when formed.

88. The balloon as recited in claim 85, wherein the first layer of material is axially compressed in the vicinity of the opening.

89. A balloon catheter, comprising:

a catheter having a first portion and a second portion;

a balloon disposed between the first portion and the second portion, the balloon comprising multiple layers of material disposed in cooperative relationship such that the balloon achieves a predefined geometry when inflated wherein at least one of the multiple layers of material is formed using a textile material and wherein the formed at least one of the multiple layers of textile material is thermally and physically treated prior to the multiple layers being disposed in cooperative relationship such that, when the multiple layers of material are disposed in cooperative relationship, the multiple layers of material will experience a change in diameter without experiencing unfolding while remaining substantially the same length without aid from a mechanical device when inflated.

90. The balloon catheter as recited in claim 89, wherein the formed at least one of the multiple layers of textile material is physically treated by being at least axially compressed.

91. The balloon catheter as recited in claim 90, wherein the textile material comprises a braided textile material.

92. The balloon catheter as recited in claim 89, wherein compliance characteristics of the multiple layers of material are independent of the predefined geometry.

93. The balloon catheter as recited in claim 89, wherein the balloon includes regions of porosity for the delivery of therapeutic agents.

* * * * *